United States Patent [19]

Yamamoto et al.

[11] Patent Number: 5,102,847
[45] Date of Patent: Apr. 7, 1992

[54] PROCESS FOR PREPARING CATALYSTS FOR PRODUCING METHACRYLIC ACID

[75] Inventors: Shinji Yamamoto; Yutaka Kinoshita; Masako Usui; Motomu Oh-Kita, all of Otake, Japan

[73] Assignee: Mitsubishi Rayon Co., Ltd., Tokyo, Japan

[21] Appl. No.: 654,990

[22] Filed: Feb. 14, 1991

[30] Foreign Application Priority Data

Feb. 15, 1990 [JP] Japan .................................. 2-032584

[51] Int. Cl.⁵ ..................... B01J 27/192; B01J 27/199
[52] U.S. Cl. .................................... 502/209; 502/205; 562/534; 562/535
[58] Field of Search ................ 502/209, 205; 562/534, 562/535

[56] References Cited

U.S. PATENT DOCUMENTS

| | | | |
|---|---|---|---|
| 4,297,247 | 10/1981 | Krabetz et al. | 502/310 |
| 4,419,270 | 12/1983 | Ueshima et al. | 502/209 |
| 4,424,141 | 1/1984 | Grasselli et al. | 502/205 |
| 4,521,618 | 6/1985 | Arntz et al. | 562/535 |
| 4,547,588 | 10/1985 | Khoobiar | 502/209 X |
| 4,558,028 | 12/1985 | Tsuneki et al. | 502/209 X |
| 4,804,778 | 2/1989 | Oh-Kita et al. | 502/209 X |
| 4,816,603 | 3/1989 | Oh-Kita et al. | 502/205 X |
| 4,954,650 | 9/1990 | Abe et al. | 562/534 |

FOREIGN PATENT DOCUMENTS

| | | |
|---|---|---|
| 0046333 | 2/1982 | European Pat. Off. |
| 0078150 | 5/1983 | European Pat. Off. |
| 1503788 | 3/1978 | United Kingdom |

OTHER PUBLICATIONS

Database WPIL, No. 85-096135, Derwent Publications, Ltd., London, GB of JP-A-60 044 042 (Ube Industries K.K.)—Abstract.

Database WPIL, No. 82-49303E, Derwent Publications, Ltd. London, GB of JP-A-57 075 147 (Ube Industries K.K.)—Abstract.

Primary Examiner—W. J. Shine
Assistant Examiner—D. J. McGinty
Attorney, Agent, or Firm—Armstrong, Nikaido, Marmelstein, Kubovcik & Murray

[57] ABSTRACT

In a process for preparing a catalyst for producing methacrylic acid represented by the formula, $$P_a Mo_b V_c Cu_d Bi_e X_f Y_g O_h$$

wherein P, Mo, V, Cu, Bi and O are phosphorus, molybdenum, vanadium, copper, bismuth and oxygen, respectively, X is at least one element selected from the group consisting of potassium, rubidium, cesium and thallium, Y is at least one element selected from the group consisting of antimony, zinc, iron, cerium, magnesium, chromium, indium, tellurium, manganese, tin, germanium, arsenic, boron, silicon, selenium, zirconium, silver, tantalum and tungsten, a, b, c, d, e, f, g and h are an atomic ratio of each element, and when b is 12, a is 0.1 to 3, c is 0.01 to 2, d is 0.01 to 2, e is 0.05 to 1, f is 0.01 to 2 and g is 0.01 to 5 and h is the number of oxygen atoms necessary to satisfy the valence of each component, the improvement comprising using at least one bismuth compound selected from the group consisting of bismuth nitrate and bismuth oxide as a source of bismuth and using nitric acid of more than 1 mole to not more than 5 moles based on 12 moles of molybdenum atoms for dissolving the bismuth compound(s).

1 Claim, No Drawings

PROCESS FOR PREPARING CATALYSTS FOR PRODUCING METHACRYLIC ACID

BACKGROUND OF THE INVENTION

1. Field of the Invention

The present invention relates to a process for preparing a catalyst used in producing methacrylic acid by the gas-phase catalytic oxidation of methacrolein.

2. Description of the Prior Art

Hitherto, a large number of catalysts containing phosphorus, molybdenum and bismuth have been reported as a catalyst for producing methacrylic acid by the gas-phase catalytic oxidation of methacrolein, for example, as shown in Japanese Patent Application Kokai No. 48-64017, No. 52-33615, No. 52-33616, No. 52-91821 and No. 53-7616. However, so far as the technical contents of these patents are looked over, every catalyst has defects that the result of reaction is poor, the catalytic activity largely lowers with the lapse of time, and the preparation of the catalyst lacks reproducibility, so that it is not said to be satisfactory as industrial catalysts. At present, therefore, a further improvement is being desired.

SUMMARY OF THE INVENTION

An object of the present invention is to provide a process for preparing a catalyst for advantageously producing methacrylic acid from methacrolein.

The present inventors have extensively studied to improve the conventional catalyst-preparation processes, and as a result have found that by adding a particular bismuth compound dissolved in a particular amount of nitric acid to a catalyst containing phosphorus, molybdenum, vanadium and copper, a catalyst superior in reproducibility and having a high activity and selectivity as an industrial catalyst can be prepared.

In a process for preparing a catalyst for producing methacrylic acid represented by the formula, $$P_a Mo_b V_c Cu_d Bi_e X_f Y_g O_h$$

wherein P, Mo, V, Cu, Bi and O are phosphorus, molybdenum, vanadium, copper, bismuth and oxygen, respectively, X is at least one element selected from the group consisting of potassium, rubidium, cesium and thallium, Y is at least one element selected from the group consisting of antimony, zinc, iron, cerium, magnesium, chromium, indium, tellurium, manganese, tin, germanium, arsenic, boron, silicon, selenium, zirconium, silver, tantalum and tungsten, a, b, c, d, e, f, g and h are an atomic ratio of each element, and when b is 12, a is 0.1 to 3, c is 0.01 to 2, d is 0.01 to 2, e is 0.05 to 1, f is 0.01 to 2 and g is 0.01 to 5 and h is the number of oxygen atoms necessary to satisfy the valence of each component, the present invention relates to the improvement comprising using at least one bismuth compound selected from the group consisting of bismuth nitrate and bismuth oxide as a source of bismuth and using nitric acid of more than 1 mole to not more than 5 moles, preferably 2 to 4.5 moles, based on 12 moles of molybdenum atoms for dissolving the bismuth compound(s).

DESCRIPTION OF THE PREFERRED EMBODIMENTS

As described above, a catalyst superior in reproducibility as an industrial catalyst can be prepared by using a particular bismuth compound dissolved in a particular amount of nitric acid.

According to the process of the present invention, methacrylic acid can be obtained from methacrolein in high yields, and particularly the catalyst obtained keeps a high catalytic activity over a long period of time, so that the industrial value of the process is extremely large.

There is no need to limit the catalyst-preparation process to a special one, but any of the known various processes such as the vaporization-to-dryness process, precipitation process, etc. may be used, so far as there is no large unbalance between the components.

Referring to materials used for the preparation of the catalyst, it is necessary to use bismuth nitrate and/or bismuth oxide as the source of bismuth. When other bismuth compounds are used, it is difficult to prepare a catalyst having a high activity and selectivity. As the sources of other metal components, the nitrate, carbonate, ammonium salt, halide, oxide, etc. of each element can be used in combination.

In preparing the catalyst, it is preferred to add a nitric acid solution of bismuth nitrate and/or bismuth oxide to a mixed solution containing catalyst components such as phosphorus, molybdenum, vanadium, copper, etc. The amount of nitric acid for dissolving the foregoing bismuth compounds is more than 1 mole to not more than 5 moles, preferably 2 to 4.5 moles based on 12 moles of molybdenum atoms. When the amount of nitric acid is outside the above range, the catalyst having a high activity and selectivity cannot be obtained.

The catalyst used in the present invention may be used without a carrier, but can also be used supported on or diluted with an inert carrier such as silica, alumina, silica-alumina, silicon carbide, etc.

The catalyst obtained according to the present invention is generally used in a fixed bed, but can also be used in a fluidized bed.

The methacrolein concentration of a gas used as a material can be changed in a wide range, but 1 to 20% by volume is suitable, and particularly 3 to 10% by volume is preferred.

Methacrolein, a material, may contain small amounts of impurities such as water, a saturated lower aldehyde, etc. These impurities give substantially no effect to the reaction.

As an oxygen source, the use of air is economical, but air made rich in pure oxygen may be used if necessary. The oxygen concentration of the gas used as a material is determined by the molar ratio to methacrolein. The value of this molar ratio is 0.3 to 4, particularly preferably 0.4 to 2.5.

The gas used as a material may be diluted with an inert gas such as nitrogen, steam, carbon dioxide, etc.

Reaction pressure is preferably atmospheric pressure to several atmospheres.

Reaction temperature can be selected from a range of 230° to 450° C., preferably 250° to 400° C.

The catalyst-preparation process of the present invention and examples of the reaction with the prepared catalyst are illustrated specifically. In the examples and comparative examples, the conversion of methacrolein and the selectivity of produced methacrylic acid are defined as follows:

$$\text{Conversion of methacrolein (\%)} = \frac{\text{Number of moles of reacted methacrolien}}{\text{Number of moles of supplied methacrolein}} \times 100$$

$$\text{Selectivity of methacrylic acid (\%)} = \frac{\text{Number of moles of produced methacrylic acid}}{\text{Number of moles of reacted methacrolein}} \times 100$$

In the following examples and comparative examples, parts are by weight, and analyses were carried out by gas chromatography.

EXAMPLE 1

50 Parts of ammonium paramolybdate, 1.38 parts of ammonium metavanadate and 2.39 parts of potassium nitrate were dissolved in 200 parts of pure water. To the resulting solution were added with stirring a solution of 4.08 parts of 85% phosphoric acid in 5 parts of pure water and then a solution of 0.57 part of copper nitrate in 5 parts of pure water. Separately, 5.80 parts of 60% nitric acid and 30 parts of pure water were added to 5.72 parts of bismuth nitrate, and the resulting uniform solution of bismuth nitrate was added to the foregoing mixed solution which was then heated to 95° C.

Thereafter, 1.03 part of antimony trioxide and 0.73 part of boric acid were added to the resulting mixed solution which was then evaporated to dryness while heating with stirring. The solid product obtained was dried at 130° C. for 16 hours, shaped by applying pressure and heat-treated at 380° C. for 5 hours under air stream. The product thus obtained was used as a catalyst.

The composition of elements except oxygen of the resulting catalyst was $P_{1.5}Mo_{12}V_{0.5}Cu_{0.1}K_1Bi_{0.5}Sb_{0.3}B_{0.5}$ (catalysts described hereinbelow also are represented by the composition of elements except oxygen). In this case, the amount of nitric acid used to dissolve the bismuth nitrate was 2.3 moles based on 12 moles of molybdenum atoms.

A tubular reactor was filled with this catalyst, and a mixed gas consisting of 5 vol.% of methacrolein, 10 vol.% of oxygen, 10 vol.% of steam and 75 vol.% of nitrogen was passed through the tubular reactor at a reaction temperature of 290° C. for a contact time of 3.6 seconds.

The product was collected and analyzed by gas chromatography to find that the conversion of methacrolien was 89.3% and the selectivity of methacrylic acid was 88.5%.

EXAMPLE 2

A catalyst having the same composition, $P_{1.5}Mo_{12}V_{0.5}Cu_{0.1}K_1Bi_{0.5}Sb_{0.3}B_{0.5}$, was prepared in the same manner as in Example 1 except that a part of bismuth nitrate was replaced by bismuth oxide, and 8.00 parts of 60% nitric acid and 50 parts of pure water were added to a mixture of 2.29 parts of bismuth nitrate and 1.65 parts of bismuth oxide, and that the resulting uniform solution of bismuth was used. In this case, the amount of nitric acid used to dissolve the bismuth compounds was 3.2 moles based on 12 moles of molybdenum atoms.

Using this catalyst, reaction was carried out under the same reaction conditions as in Example 1 to find that the conversion of methacrolein was 89.1% and the selectivity of methacrylic acid was 88.4%.

EXAMPLE 3

A catalyst having the same composition, $P_{1.5}Mo_{12}V_{0.5}Cu_{0.1}K_1Bi_{0.5}Sb_{0.3}B_{0.5}$, was prepared in the same manner as in Example 1 except that 2.75 parts of bismuth oxide was replaced by bismuth nitrate, and 10.03 parts of 50% nitric acid and 50 parts of pure water was added to the bismuth oxide, and that the resulting uniform solution of bismuth oxide was used. In this case, the amount of nitric acid used to dissolve the bismuth oxide was 3.4 moles based on 12 moles of molybdenum atoms.

Using this catalyst, reaction was carried out under the same reaction conditions as in Example 1 to find that the conversion of methacrolein was 88.7% and the selectivity of methacrylic acid was 89.0%.

EXAMPLES 4 to 13

Catalysts shown in Table 1 were prepared according to Example 1. Using these catalysts, reaction was carried out under the same conditions as in Example 1 to obtain results shown in Table 1.

TABLE 1

| Example | Composition of catalyst (atomic ratio) | Source of bismuth | Amount of nitric acid $HNO_3/Mo_{12}$ (mole/mole) | Conversion of methacrolein (%) | Selectivity of methacrylic acid (%) |
|---|---|---|---|---|---|
| 4 | $P_{1.5}Mo_{12}V_{0.5}Cu_{0.1}K_1Bi_{0.3}Sb_{0.5}Fe_{0.2}$ | Bismuth nitrate | 2.0 | 90.3 | 87.5 |
| 5 | $P_{1.5}Mo_{12}V_{0.5}Cu_{0.1}Cs_1Bi_{0.3}Sb_{0.3}Zn_{0.2}Ge_{0.1}$ | Bismuth nitrate | 3.0 | 90.0 | 88.0 |
| 6 | $P_{1.5}Mo_{12}V_{0.8}Cu_{0.1}K_{0.7}Cs_{0.4}Bi_{0.3}Sb_{0.3}Ge_{0.2}As_{0.2}$ | Bismuth oxide | 2.5 | 90.1 | 89.0 |
| 7 | $P_1Mo_{12}V_{0.8}Cu_{0.2}Tl_{0.8}Bi_{0.5}Sb_{0.1}Mg_{0.2}Si_{0.1}$ | Bismuth nitrate + bismuth oxide | 2.5 | 89.6 | 87.6 |
| 8 | $P_1Mo_{12}V_{0.5}Cu_{0.2}Rb_1Bi_{0.3}Sb_{0.3}Cr_{0.2}Te_{0.2}$ | Bismuth oxide | 4.0 | 89.9 | 87.5 |
| 9 | $P_1Mo_{12}V_{0.5}Cu_{0.2}Rb_{0.5}Tl_{0.3}Bi_{0.3}Ce_{0.2}Mn_{0.1}$ | Bismuth nitrate | 3.5 | 91.1 | 87.3 |
| 10 | $P_{1.5}Mo_{12}V_{0.5}Cu_{0.2}Cs_1Bi_{0.2}Ce_{0.2}Se_{0.1}Ag_{0.05}$ | Bismuth nitrate + bismuth oxide | 2.0 | 91.3 | 87.2 |
| 11 | $P_{1.5}Mo_{12}V_{0.8}Cu_{0.1}K_1Bi_{0.3}In_{0.1}Ta_{0.2}$ | Bismuth nitrate | 2.5 | 90.0 | 87.4 |
| 12 | $P_{1.5}Mo_{12}V_{0.8}Cu_{0.1}K_1Bi_{0.5}Sb_{0.3}W_{0.1}Zr_{0.05}$ | Bismuth oxide | 2.5 | 90.5 | 87.4 |
| 13 | $P_{1.5}Mo_{12}V_{0.8}Cu_{0.1}K_1Bi_{0.3}Sb_{0.5}Fe_{0.2}Sn_{0.1}$ | Bismuth oxide | 2.5 | 90.7 | 87.3 |

COMPARATIVE EXAMPLE 1

A comparative catalyst having a composition, $P_{1.5}Mo_{12}V_{0.5}Cu_{0.1}K_1Bi_{0.5}Sb_{0.3}B_{0.5}$, was prepared according to Example 1 except that no nitric acid was used to dissolve bismuth nitrate. Using this catalyst, reaction was carried out under the same reaction conditions as in Example 1 to find that the conversion of methacrolein was 89.0% and the selectivity of methacrylic acid was 86.5%.

COMPARATIVE EXAMPLE 2

A comparative catalyst having a composition, $P_{1.5}Mo_{12}V_{0.5}Cu_{0.1}K_1Bi_{0.5}Sb_{0.3}B_{0.5}$, was prepared according to Example 1 except that the amount of nitric acid used to dissolved bismuth nitrate was 6.0 moles based on 12 moles of molybdenum atoms. Using this catalyst, reaction was carried out under the same reaction conditions as in Example 1 to find that the conversion of methacrolein was 87.0% and the selectivity of methacrylic acid was 87.3%.

What is claimed is:

1. In a process for preparing a catalyst for producing methacrylic acid represented by the formula, $$P_aMo_bCu_dBi_eX_fY_gO_h$$

wherein, P, Mo, V, Cu, Bi and O are phosphorus, molybdenum, vanadium, copper, bismuth and oxygen, respectively, X is at least one element selected from the group consisting of potassium, rubidium, cesium and thallium, Y is at least one element selected from the group consisting of antimony, zinc, iron, cerium, magnesium, chromium, indium, tellurium, manganese, tin, germanium, arsenic, boron, silicon, selenium, zirconium, silver, tantalum and tungsten, a, b, c, d, e, f, g and h are an atomic ratio of each element, and when b is 12, a is 0.1 to 3, c is 0.01 to 2, d is 0.01 to 2, e is 0.05 to 1, f is 0.01 to 2 and g is 0.01 to 5 and h is the number of oxygen atoms necessary to satisfy the valence of each component, the improvement comprising using at least one bismuth compound selected from the group consisting of bismuth nitrate and bismuth oxide as a source of bismuth and using nitric acid of more than 1 mole to not more than 5 moles based on 12 moles of molybdenum atoms for dissolving the bismuth compound(s).

* * * * *